United States Patent [19]
Wesseler

[11] Patent Number: 5,534,228
[45] Date of Patent: Jul. 9, 1996

[54] CONNECTOR SYSTEM FOR CONNECTING LIQUID CONTAINERS

[75] Inventor: Matthias Wesseler, Melle, Germany

[73] Assignee: Fresenius AG, Bad Homburg von der Hohe, Germany

[21] Appl. No.: 228,802

[22] Filed: Apr. 14, 1994

[30] Foreign Application Priority Data

Apr. 26, 1993 [DE] Germany .......................... 43 13 636.2

[51] Int. Cl.⁶ ..................................................... A61B 19/00
[52] U.S. Cl. ........................... 422/103; 604/403; 604/416
[58] Field of Search ...................................... 604/256, 283, 604/403, 905, 416; 422/103, 99, 100; 128/912, 917

[56] References Cited

U.S. PATENT DOCUMENTS

| 4,614,437 | 9/1986 | Buehler ............................... 604/414 X |
| 5,113,571 | 5/1992 | Manska ...................................... 29/453 |
| 5,152,965 | 10/1992 | Fisk et al. ............................ 422/103 X |
| 5,251,873 | 10/1993 | Atkinson et al. ................... 604/256 X |
| 5,292,308 | 3/1994 | Ryan .................................... 604/905 X |
| 5,322,518 | 6/1994 | Schneider et al. ...................... 604/247 |

FOREIGN PATENT DOCUMENTS

| 0257880 | 3/1988 | European Pat. Off. . |
| 0510854 | 10/1992 | European Pat. Off. . |
| 0512281 | 11/1992 | European Pat. Off. . |
| 0511538 | 11/1992 | European Pat. Off. . |
| 3618739 | 12/1986 | Germany . |
| 3627231 | 2/1988 | Germany . |
| 4223062 | 1/1994 | Germany . |

Primary Examiner—Jeffrey R. Snay
Attorney, Agent, or Firm—Panitch Schwarze Jacobs & Nadel

[57] ABSTRACT

A connector system for the connection of liquid reservoirs or containers is configured in such a way that a predetermined connection sequence must be followed. For this purpose, the system has two connecting pieces (1, 2) each of which is provided with two connectors (1A, 1B, 2A, 2B), the first connectors (1A, 2A) serving to connect containers of liquid (BI, BII). The configuration of the connectors allows the two connecting pieces to be connected together by means of a specially configured intermediate piece (3), but on the other hand does not allow connection of one of the connecting pieces with a third container. The preferred area of application of the connector system is medical technology, for example the transfer of liquids during hemofiltration.

13 Claims, 4 Drawing Sheets

CONNECTOR SYSTEM FOR CONNECTING LIQUID CONTAINERS

FIELD OF THE INVENTION

The invention relates to a connector system for the connecting of containers or reservoirs of liquid, and in particular containers for medical liquids.

BACKGROUND OF THE INVENTION

In medical technology, but in other areas as well, such as in laboratories, it is often necessary to transfer liquids from one container into another in a specific sequence, and then to transport them further after a certain period of time or after a predetermined interval, for example a mixing or a chemical reaction.

Dialysis according to the hemofiltration procedure can be mentioned as one example. In this procedure, a bicarbonate-electrolyte solution is used as the medium. Since the two individual solutions, i.e., the bicarbonate solution and the electrolyte solution, can only be kept in a mixed state for 24 hours, they are stored in separate bags and not mixed until just before their application. Since transfer to the patient of only one of the two components can be critical, provisions have to be made to ensure that in every instance, before connection to a transfusion set, the two solutions are mixed together and that an inadvertent connection of just one of the solution components is avoided through effective precautions.

In the area of application mentioned above, it is known that the two solutions are to be stored separately from each other in two separate bags, and only mixed together immediately before use. This system does not, however, exclude the possibility that as a result of inattentive operation, the combining and mixing is neglected, and only one of the components is dispensed into the transfusion set.

A system of that type has become known, for example, from DE-36 27 231 A1, in which is described a so-called transfer device for the mixing of medicines located in two different containers. However, this system still retains exactly that disadvantage described above. Indeed, there is in this reference a description of a temporal sequence for effecting the connection between the two containers. However, this is not against the background that this connection must be carried out in an absolutely essential temporal sequence.

In addition, it is known that both solutions can be stored separated by a wall in a double-chamber bag. When this is done, the permissible storage period is determined by the component that can be kept for the shorter period, so that if the expiration date has passed, the other component, which by itself would still be usable, is lost as well. Furthermore, with a double-chamber bag, two liquids are always allocated to each other in specific quantity and concentration, so that in storage the appropriate pairing for each combination must be retained.

SUMMARY OF THE INVENTION

Against this background, it is the object of the present invention to create a connector system which, due to its construction, permits only a single predetermined connection sequence for the containers of liquid and excludes the possibility of incorrect operation. In addition, the system should also make it possible to connect together containers of liquid that have been filled and stored independently of one another. At the same time, stringent requirements must be met with regard to the tightness of the connections.

The above objects are achieved with the connector system according to the invention, which comprises—with the generic system—two connecting pieces, each of which can be connected to one container of liquid. In accordance with the invention, the connecting pieces can be connected with each other only through the use of an intermediate piece, so that in this way, the liquid can be transferred from one container into the other, whereby the two liquids are mixed or possibly react with one another.

In accordance with the invention, the above-mentioned intermediate piece permits, first of all, the connecting together of the two connecting pieces. In addition, this intermediate piece permits a connection of one of the containers to an additional container or to a line, and specifically, after removal of one of the connecting pieces by attachment of a connection piece of the additional container or the additional line. For this purpose, the intermediate piece is detachably connected with the first connecting piece, and non-detachably connected with the second. In this way, it is conclusively predetermined that the liquid from the first container is first transferred into the second container, that the intermediate piece is then detached from the first container but remains connected with the second container, and that only then can the liquid be transferred from the second container into an additional container or into a line.

The first connecting piece is configured, for example, as a conventional male Luer lock connector. In conjunction with this, the intermediate piece is at first placed on the inside of the first connecting piece. In this way, the connection of the first connecting piece to a conventional female Luer lock piece is prevented. A connection is possible only with the second connecting piece of the inventive connection system.

Following disconnection of the first connecting piece and the intermediate piece, the intermediate piece is located in the interior of the second connecting piece as a result of which a connection of the second connecting piece is only then made possible with a conventional male Luer lock piece of an additional container or an additional line, for example a transfusion set.

In conjunction with this, the intermediate piece is equipped with a check valve that prevents a backflow of the liquid into the first container when, after effecting the connection, this liquid flows through the connector system from the first container to mix with the liquid in the second container. A check valve for the connection of two parts for use in the medical arts is known, for example, from EP 0 257 880 A1. However, there is no teaching in this reference with regard to a definite temporal sequence to the connections, while in the present case, the temporal sequence is necessarily determined by the intermediate piece.

If the liquid mixture is now to be supplied from the second container, the intermediate piece is detached from the first connecting piece at the location of the detachable connection, mentioned above, and a connection is then made with a tube system, for example. When this is done, the connection takes place along with the removal of the blocking effect of the check valve in the intermediate piece. That is, liquid can now flow in the reverse direction through the intermediate piece from the second container, which contains the liquid mixture to be applied, to a connected line that leads, for example, to a transfusion set.

BRIEF DESCRIPTION OF THE DRAWINGS

The foregoing summary, as well as the following detailed description of a preferred embodiment of the invention, will be better understood when read in conjunction with the appended drawings which show further features and advantages of the invention. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF PREFERRED EMBODIMENT

The embodiment of the present invention described below is a system for mixing of two solutions for a hemofiltration procedure and for connection of the mixture to a transfusion set. In the figures, the same parts are always provided with the same reference numbers.

Figure 1:
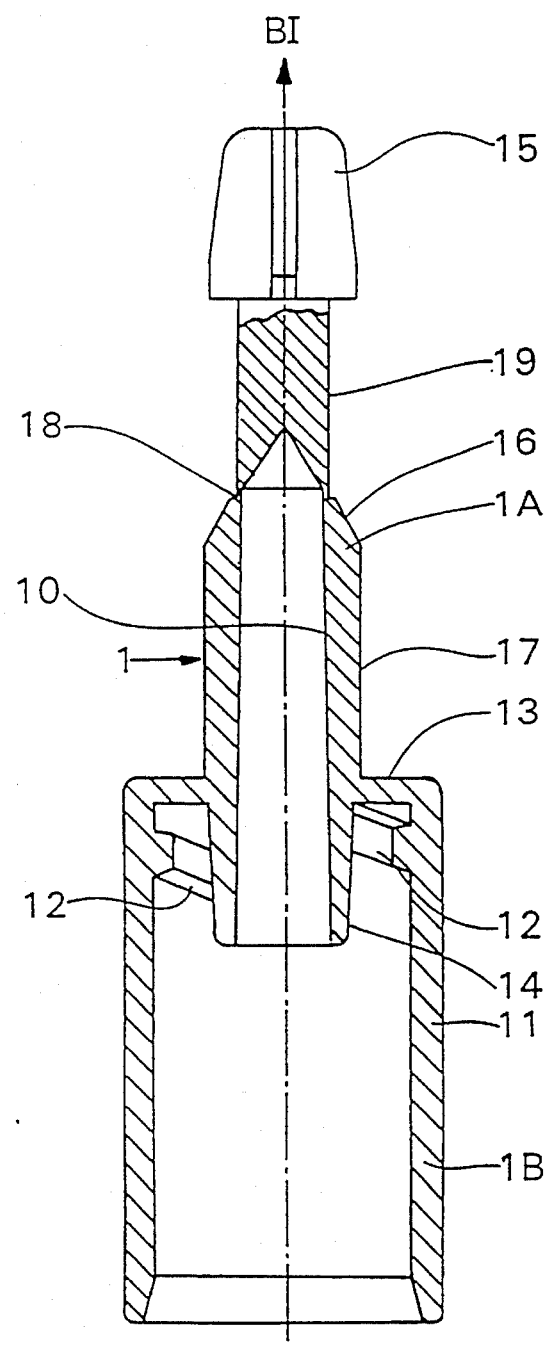
FIG. 1 shows the first connecting piece in longitudinal cross-section.
Figure 2:
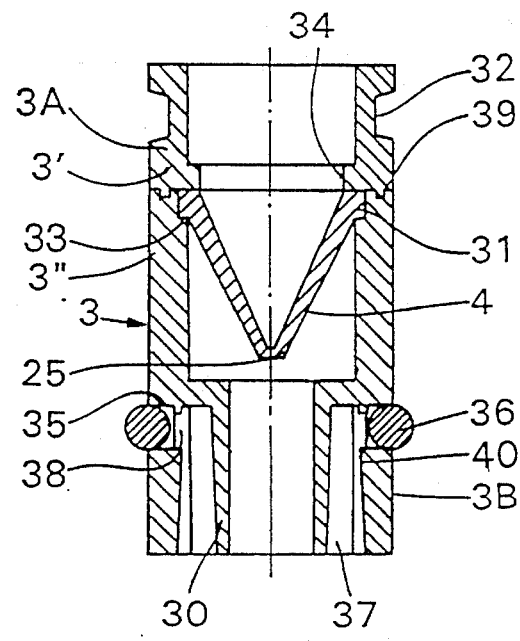
FIG. 2 shows the intermediate piece in longitudinal section.
Figure 3:
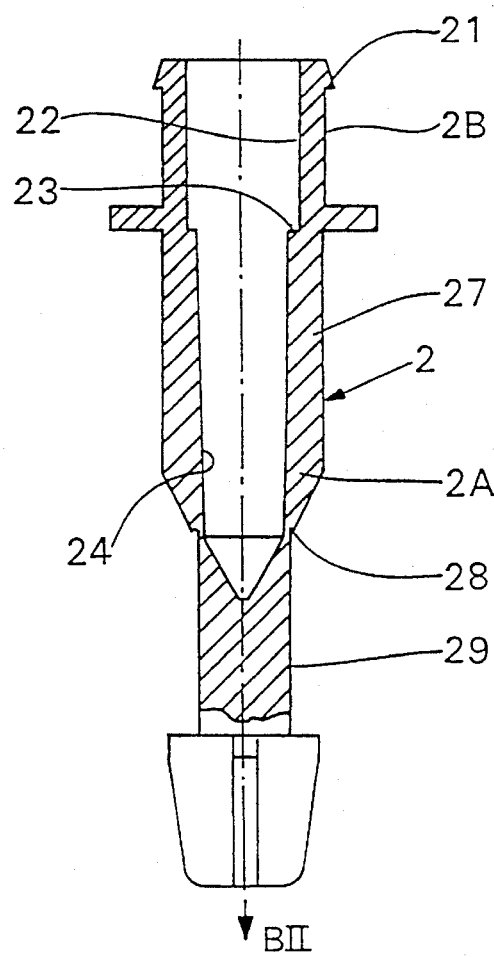
FIG. 3 shows the second connecting piece in longitudinal cross-section.

In FIGS. 1 through 3 the three parts are shown which comprise the connector system in accordance with the invention namely, a first connecting piece 1, a second connecting piece 2, and an intermediate piece 3. The first connecting piece 1 has a first connector 1A and a second connector 1B, in the same way, the second connecting piece 2 possesses a first connector 2A and a second connector 2B. The two connectors 1A and 2A serve for connecting the respective connection pieces at BI and BII to bag-like containers (not shown), one of which contains a bicarbonate solution and the other of which contains an electrolyte solution.

The connector 1A is configured as a hollow, cylindrically shaped body or tubular segment 17, whose first end terminates as a break-off piece 19 along a predetermined breaking point 18. At its other end the break-off piece 19 has a number of vanes 15 that are intended to come into frictional contact with the inner wall of a tubing which is slipped over the tubular segment 17, so that the piece that is broken off is then not supposed to slip back on the tubular segment 17.

The hollow, cylindrically shaped body or the tubular segment 17 itself on the end opposite the predetermined breaking point 18 has the outer contour of a cone 14, which projects into an outer sleeve 11 that is formed on the tubular segment 17 and is enclosed by this outer sleeve. The outer sleeve 11 is itself configured as a hollow cylinder and, in the region lying opposite the cone 14 of the tubular segment 17, has a first screw arrangement in the form of short screw threads 12 that protrude to the inside. One end of the outer sleeve 11 is closed off by means of a ring plate 13, which is penetrated by the hollow cylindrical body 17, while the other, open end forms the second connector 1B.

In use, a tube (not shown), which leads to a bag (not shown) at BI with a first solution, is pushed over the tubular segment 17 up to the ring plate 13 of the outer sleeve 11. The connectors 1A and 1B are thus coaxial with one another, and are connected with each other by means of a through channel 10.

The intermediate piece 3 shown in FIG. 2 has two connectors 3A and 3B. The connector 3A, with its generally cylindrical shape, fits into the outer sleeve 11 of the connector 1B of the first connecting piece 1, and has at its end an outer thread 32 that engages with the screw threads 12 of connector 1B.

The intermediate piece 3 essentially comprises two hollow cylindrical sections 3', 3", whereby the outer diameter of the two sections 3', 3" is somewhat smaller than the inner diameter of the outer sleeve 11 of the first connecting piece 1, so that the intermediate piece 3—as mentioned above—can be pushed into this outer sleeve 11. In conjunction with this, the length of the intermediate piece 3 is dimensioned in such a way that, following insertion and the production of the screw connection in the outer sleeve 11, the intermediate piece 3 terminates basically flush with this outer sleeve at the connector 1B.

At the end of the first section 3' opposite the entry end, a ring-like narrowing 34 is provided, which serves as a support block for a hollow cone-shaped check valve 4. This check valve 4 has at its base a ring-shaped flange 31, from which the surfaces of the hollow cone extend in a tapering, cone-like manner to the tip 25. The tip 25 is itself provided with a slit that opens under pressure from the hollow cone side. This check valve 4 is made from a flexible material, preferably silicone.

To the first section 3' of the intermediate piece 3, a second section 3" is attached, for example by welding. In the area of the welding seam 39, there is set into the inner surface of the second section 3" a ring groove 33 into which the ring-shaped flange 31 of the check valve 4 is inserted. When the two sections 3', 3" are assembled, this ring flange 31 is compressed axially and thus becomes securely seated. In addition, this also leads to an outstanding sealing of the intermediate piece 3. In conjunction with this, the diameter of the opening in the ring flange 31 is so dimensioned that it comes to rest in a sealing fashion with an additional tubular connection piece, described more fully below, of an additional bag or a transfusion system.

In this regard, the tip 25 of the check valve 4 is directed towards the end of the intermediate piece 3 that is opposite the screw thread 32 and if no additional connector is installed, allows liquid to flow only in this direction, that is from connector 3A to connector 3B.

In addition, the second section 3" of the intermediate piece 3 also has on its outer surface a ring-like groove 35 into which a ring seal, preferably an O-ring 36, is inserted. When the intermediate piece 3 is connected with the first connecting piece 1, this O-ring 36 comes into sealing contact with the inner surface of the outer sleeve 11, and thereby seals the entire first connection assembly.

At about the level of the ring groove 35 and set into the inner surface of the hollow, cylindrical second section 3" are two opposed openings 38 and that are linked by means of grooves 37 that extend axially from the entry opening of the second section 3" to these openings 38.

At a distance from the entry opening, there is placed concentrically inside the second section 3" a tubular segment 30, which has a small wall diameter, that is joined with the inner wall of the second section 3" above the two openings 38. At the same time, the outer diameter of this tubular segment 30 is so dimensioned that it can be inserted into the expanded entry opening 22 of the second connecting piece 2, which will be explained in more detail below.

Figure 4:
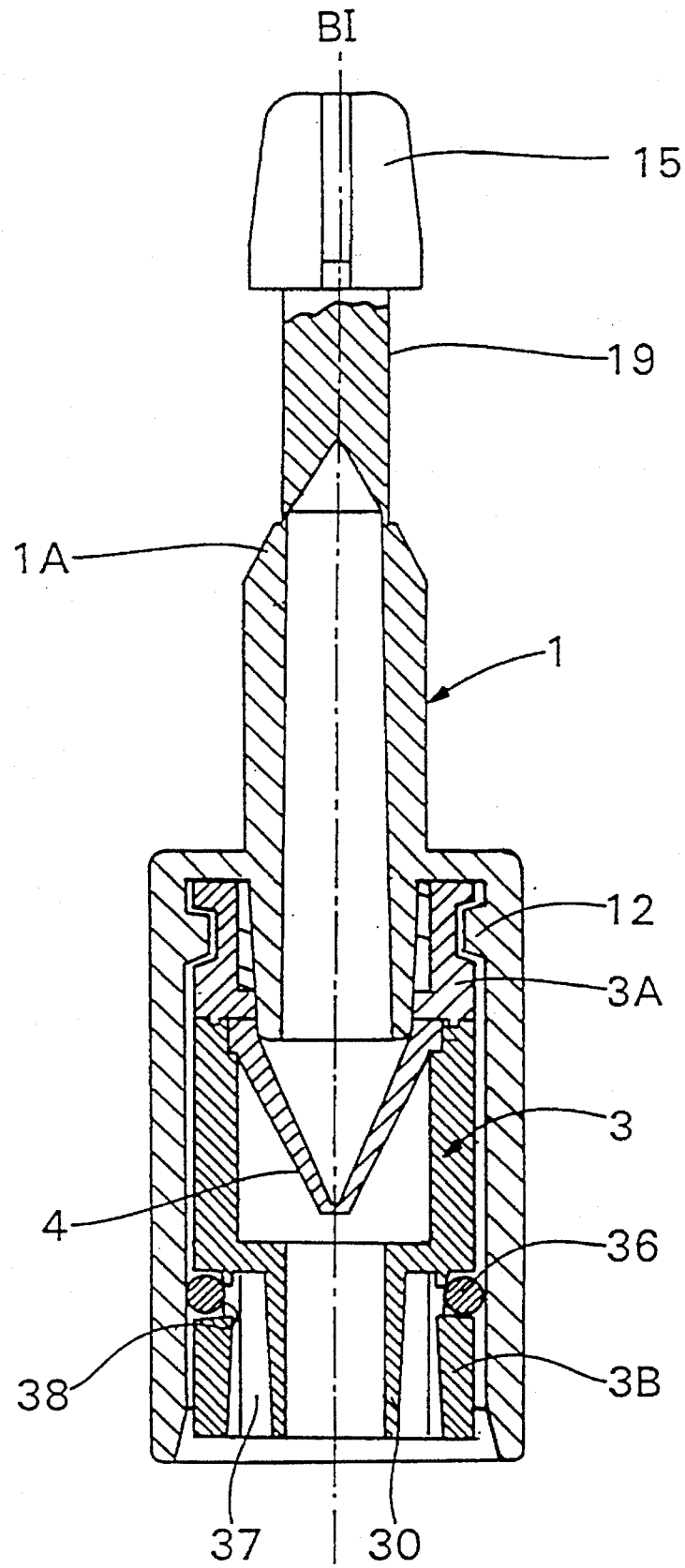
FIG. 4 shows the first connecting piece with intermediate piece attached to it, both in longitudinal cross-section.

FIG. 4 shows in a very clear way the connecting piece 1 with the intermediate piece 3 inserted into it. With pieces 1 and 3 joined together in this way, the connector system is ready for use for connection with the connecting piece 2, which is shown in FIG. 3.

The second connecting piece 2 like connecting piece 1, has a hollow, cylindrical body or tubular segment 27, the first end of which is joined with a break-off piece 29 along a predetermined breaking point 28, which is configured in the same way as break-off piece 19 of the first connecting piece 1. The section of the tubular segment 27 that faces the break-off piece 29 forms connector 2A of the connecting piece 2.

Figure 5:
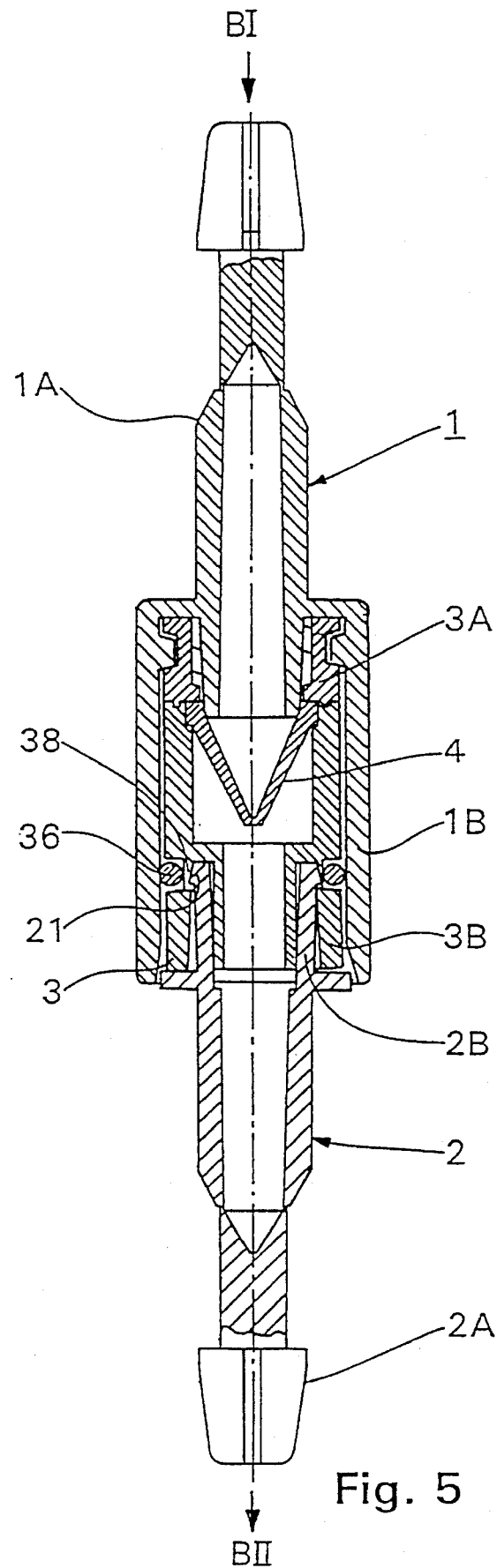
FIG. 5 shows the first connecting piece, the intermediate piece, and the second connecting piece, all connected together and shown in longitudinal cross-section.

The opposite connector 2B has along its outer circumference two opposing lugs 21 that pass through the above-described axial grooves 37 of the intermediate piece 3. The flow channel 22 of the second connecting piece 2 is widened at its connector 2B and, while forming a shoulder 23 that narrows radially inwardly, leads into a through flow channel 24 of constant diameter. However, the above-mentioned shoulder 23 is configured in such a way that, upon connection, it cooperates with the tubular segment 30 of the intermediate piece 3 in an interlocking fashion, and compresses this tubular segment 30, which can be radially deformed due to its thin wall thickness. When the second connecting piece 2 is pushed into the intermediate piece 3, the lugs 21 ride over a radial narrowing 40 before reaching the two openings 38, snap into these two openings 38 after passing this narrowing 40, and thus permanently and non-detachably lock the second connecting piece 2 into the intermediate piece 3. The locked connection between the connecting piece 2 and the intermediate piece 3 can be seen in the lower part of FIG. 5.

As already explained above, the first connecting piece 1 is first connected with the intermediate piece 3, whereby the intermediate piece is interlockingly inserted into the first connecting piece. This assembly is then closed off with a cap (not shown) and finally connected with the tube at B1 to a first bag, as mentioned above. The second connecting piece 2 is connected with another bag assembly at BII.

In order to mix the contents of the two bags, the first connection assembly, comprising the first connecting piece 1 and the intermediate piece 3, is connected with the second connecting piece 2. Next, both break-off pieces 19 and 29 are broken off, so that a through flow channel exists, from one bag at BI to the other bag at BII. The channel is closed off only by the check valve 4, which only allows flow to take place from the first connecting piece 1 to the second connecting piece 2. Once both bags are internally mixed with one another, the first connecting piece 1 can then be unscrewed from the intermediate piece 3, while the intermediate piece 3, because of its frictional and positive connection, remains with the second connecting piece 2. Into the second connection assembly, which has now been formed from the second connecting piece 2 and the intermediate piece 3, a third connecting piece 6 (see FIG. 6) with a tubular segment 64 can be inserted. This connecting piece 6 is so dimensioned that it thrusts through the hollow cone of check valve 4 while opening the valve. Thereafter, the bag contents can be transferred from the second bag in accordance with instructions.

Figure 6:
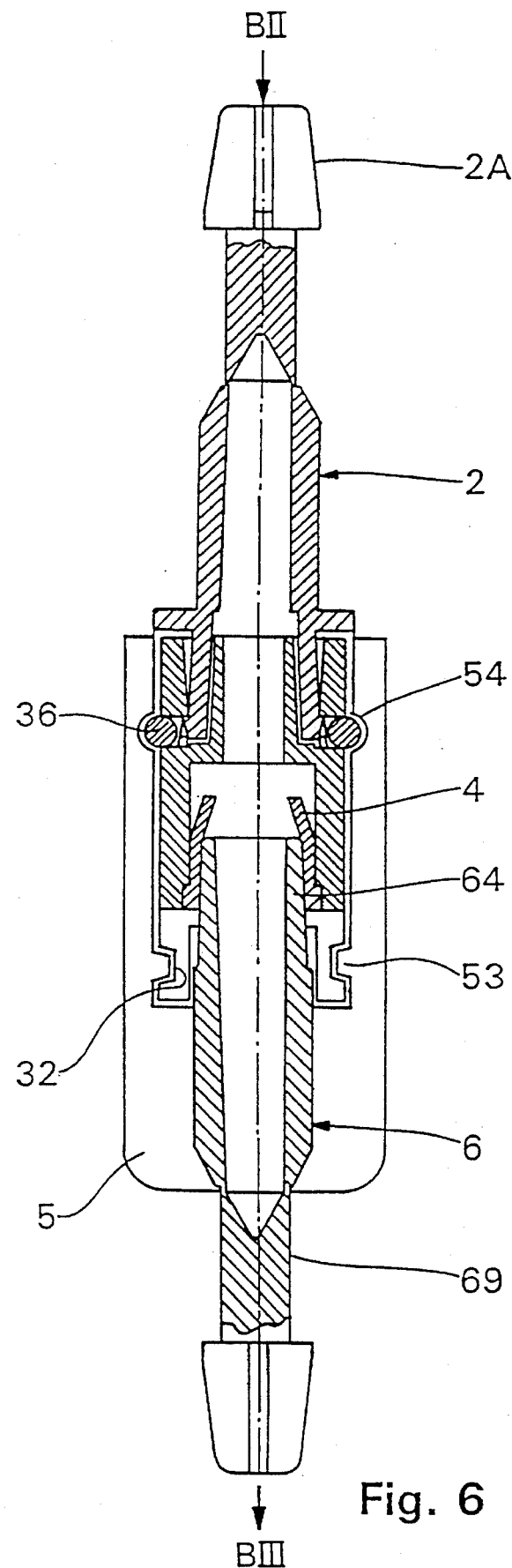
FIG. 6 shows the second connecting piece with intermediate piece attached to it and with a connector of the connection system, all shown in longitudinal cross-section.

Also in FIG. 6 can be seen a sleeve 5, which overlaps connecting piece 6 in the manner of an external coupling sleeve. The sleeve 5 is so configured on its inside that screw threads 53 are provided, which can be screwed together with the already-described screw thread 32 of the first section 3' of the intermediate piece 3.

The sleeve 5 is so dimensioned that it overlaps the second connection assembly, comprising the second connecting piece 2 and the intermediate piece 3, to such an extent that it at least overlaps the O-ring 36 of the intermediate piece 3 when the sleeve 5 is screwed together with the intermediate piece 3. At the level of the O-ring 36, which now seals against the inner surface of the sleeve 5, there is set into the inner surface of the sleeve 5 a ring-shaped groove 54 in which the O-ring 36 comes to rest. In this way, the sleeve 5 completely seals the second connection assembly.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

I claim:

1. A connector system for connecting liquid containers together and to a receiver for liquid from said containers in a predetermined connection sequence comprising;

first and second connecting pieces, each of said connecting pieces having a first connector at one end, a second connector at the opposite end, and a longitudinal bore for enabling fluid flow through each said connecting piece, said first connector being configured for connection to at least one of said liquid containers, an intermediate connecting piece having a first intermediate connector at one end, a second intermediate connector at the opposite end, and a longitudinal bore for enabling fluid flow through said intermediate connecting piece, and a connection fitting for a liquid receiver, said connection fitting comprising a longitudinal bore for enabling fluid flow therethrough and being configured for detachable connection to said first intermediate connector of said intermediate connecting piece, wherein said first connector of each of said first and second connecting pieces is configured for connection to at least one of said liquid containers, said second connector of said first connecting piece is configured for detachable connection to said first intermediate connector of said intermediate connecting piece, said second connector of said second connecting piece is configured for non-detachable connection to said second intermediate connector of said intermediate connecting piece, and said second connector of each of said first and second connecting pieces is configured such that connection of said first and second connecting pieces is enabled exclusively by the intermediate connecting piece, further wherein said intermediate connecting piece is disposed inside said first connecting piece by connection of said first intermediate connector to said second connector of said first connecting piece, such that removal of the intermediate connecting piece from said first connecting piece prior to attachement of said second connecting piece to said second intermediate connector of said intermediate connecting piece is precluded.

2. A connector system in accordance with claim 1, wherein the first and the second connectors (1A, 2A, 3A, 1B, 2B, 3B) of the first and second connecting pieces (1, 2) and the intermediate piece (3) are arranged coaxially when connected together.

3. A connector system in accordance with claim 1, wherein the second connector (1B) of the first connecting piece (1) and the first intermediate connector (3A) of the intermediate piece (3) are configured as mating screw threads.

4. A connector system in accordance with claim 1, wherein the connection between the second connector (2B) of the second connecting piece (2) and the second intermediate connector (3B) of the intermediate piece (3) are configured to form a non-detachable latching connection.

5. A connector system in accordance with claim 1, wherein the first intermediate connector (3A) of the intermediate piece (3) is configured on its outside for connection with the second connector (1B) of the first connecting piece (1), and on its inside as a female Luer cone for connection with the connection fitting (6) for a liquid receiver.

6. A connector system in accordance with claim 1, wherein said liquid receiver comprises a transfusion set.

7. A connector system in accordance with claim 1, wherein at least one of said first and second connecting pieces has a break-off piece (19,29) on its first connector (1A,2A) for insertion into a tubular line for a liquid container.

8. A connector system in accordance with claim 1, wherein the intermediate piece (3) has a check valve (4) that enables flow of liquid from the first intermediate connector (3A) to the second intermediate connector (3B) of the intermediate piece (3), but prevents flow of liquid from the second intermediate connector (3B) to the first intermediate connector (3A) when the intermediate piece (3) is connected with the first connecting piece (1).

9. A connector system in accordance with claim 8, wherein the check valve (4) is forcibly opened when the first intermediate connector (3A) is connected with said connection fitting (6), thereby enabling flow of liquid from the second intermediate connector (3B) to the first intermediate connector (3A) and then through the connection fitting (6) to a liquid receiver.

10. A connector system in accordance with claim 8, wherein the check valve (4) of the intermediate piece (3) comprises a female Luer cone and is opened by a male Luer cone provided in the connection fitting (6) when the intermediate piece (3) is connected to the connection fitting (6).

11. A connector system in accordance with claim 1, wherein said first connectors of said first and second connecting pieces include means to connect to containers of medical liquid.

12. A connector system in accordance with claim 11, wherein the system includes means for mixing liquids from said containers to provide a mixed liquid and means for transferring the mixed liquid to a liquid receiver through said connection fitting.

13. The connector system of claim 11, wherein said means to connect to containers comprises a tube.

* * * * *